United States Patent
Petitpierre

[11] 4,132,714
[45] Jan. 2, 1979

[54] PRODUCTION OF CHROMENOINDOLE COMPOUNDS

[75] Inventor: Jean C. Petitpierre, Kaiseraugst, Switzerland

[73] Assignee: Ciba-Geigy Corporation, Ardsley, N.Y.

[21] Appl. No.: 799,062

[22] Filed: May 20, 1977

[30] Foreign Application Priority Data

Feb. 25, 1977 [CH] Switzerland ............ 2395/77

[51] Int. Cl.² ........................... C07D 209/80
[52] U.S. Cl. .................. 260/326.5 B; 544/60; 544/80; 544/121; 544/129; 544/142; 544/360; 544/357; 544/372; 546/187; 546/198
[58] Field of Search ............ 260/326.5 B, 293.58, 260/268 PC; 544/142, 60, 80, 121, 129, 357, 360, 372

[56] References Cited

U.S. PATENT DOCUMENTS

| 3,929,829 | 12/1975 | Borror | 260/326.15 |
| 3,976,659 | 8/1976 | Borror | 260/326.15 |

*Primary Examiner*—Jose Tovar
*Attorney, Agent, or Firm*—Edward McC. Roberts; Prabodh I. Almaula

[57] ABSTRACT

A new process for the manufacture of a chromenoindole compound of the general formula

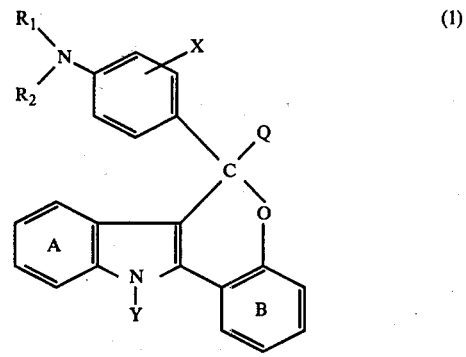

which process comprises reacting a carbinol compound of the general formula

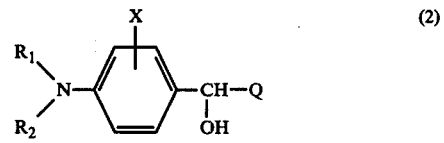

with a (2-(2'-hydroxyphenyl)-indole compound of the general formula

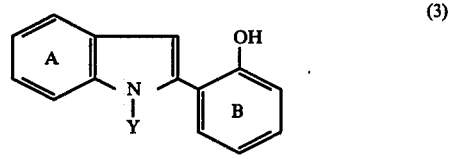

and oxidizing the reaction product to a compound of the formula (1).

10 Claims, No Drawings

PRODUCTION OF CHROMENOINDOLE COMPOUNDS

The present invention relates to a process for the manufacture of chromenoindole compounds of the general formula

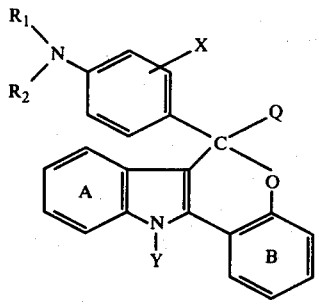

in which $R_1$ and $R_2$ indpendently of one another denote hydrogen, alkyl which has at most 12 carbon atoms and is unsubstituted or substituted by halogen, hydroxyl, cyano or lower alkoxy, cycloalkyl, phenyl, benzyl or phenyl or benzyl which are substituted by halogen, lower alkyl or lower alkoxy, or $R_1$ and $R_2$, together with the nitrogen atom which links them, denote a 5-membered or 6-membered, preferably saturated, heterocyclic radical, Q denotes hydrogen, lower alkyl, benzyl or the groups of the formulae (1a) or (1b)

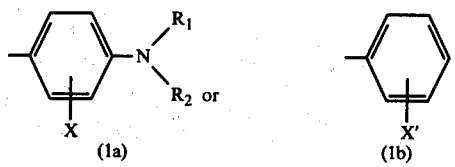

X and X' each denote hydrogen, halogen, lower alkyl or lower alkoxy, Y denotes hydrogen, alkyl with 1 to 12 carbon atoms, phenyl or benzyl and the rings A and B independently of one another can be further substituted by halogen, nitro, lower alkyl, lower alkoxy, phenyl, phenoxy or an amino group which is optionally substituted by lower alkyl, phenyl or benzyl.

The new process is characterised in that a carbinol compound of the general formula

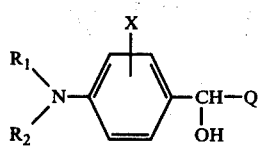

in which $R_1$, $R_2$, X and Q have the indicated meaning, is reacted with a 2-(2'-hydroxyphenyl)-indole compound of the general formula

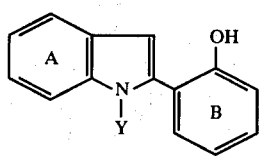

in which A, B and Y have the indicated meaning, and the reaction product is oxidised to a compound of the formula (1).

In the definition of the radicals of the chromenoindole compounds and of the starting materials of the formulae (2) and (3), lower alkyl and lower alkoxy as a rule represent those groups which contain 1 to 5 and especially 1 to 3 carbon atoms, such as, for example, methyl, ethyl, n-propyl, isopropyl, n-butyl, sec.-butyl, tert.-butyl or amyl and methoxy, ethoxy or isopropoxy.

If the substituents $R_1$, $R_2$ and Y represent alkyl groups, these can be straight-chain or branched alkyl radicals. Examples of such alkyl radicals are methyl, ethyl, n-propyl, isopropyl, n-butyl, sec.-butyl, n-hexyl, n-octyl or n-dodecyl.

If the alkyl radicals in $R_1$ and $R_2$ are substituted, they are, above all, cyanoalkyl, halogenoalkyl, hydroxyalkyl or alkoxyalkyl, each with 2 to 4 carbon atoms, such as, for example, $\beta$-cyanoethyl, $\beta$-chloroethyl, $\beta$-hydroxyethyl, $\beta$-methoxyethyl or $\beta$-ethoxyethyl.

Examples of cycloalkyl in the meaning of the R radicals are cyclopentyl or, preferably, cyclohexyl.

Preferred substituents in the benzyl and phenyl group of the R radicals are, for example, halogens, methyl or methoxy. Examples of araliphatic and aromatic radicals of this type are p-methylbenzyl, o- or p-chlorobenzyl, o- or p-tolyl, xylyl, o-, m- or p-chlorophenyl or o- or p-methoxyphenyl.

If the substituents $R_1$ and $R_2$, together with the common nitrogen atom, represent a heterocyclic radical, this is, for example, pyrrolidino, piperidino, pipecolino, morpholino, thiomorpholino or piperazino.

The substituents $R_1$ and $R_2$ are preferably benzyl or lower alkyl. The N-substituent Y is, in particular, hydrogen, phenyl, benzyl or alkyl with 1 to 8 carbon atoms, for example n-octyl or, above all, methyl or ethyl.

The radical Q advantageously denotes the group (1a). X and X' are preferably hydrogen or also halogen, methyl, methoxy or ethoxy.

The rings A and B are preferably not further substituted or independently of one another are further substituted by halogen, lower alkyl or lower alkoxy, for example by chlorine, methyl, tert.-butyl or methoxy. The ring B can also carry a phenyl radical or an amino group, which is optionally substituted by lower alkyl, especially by methyl or ethyl.

Chromenoindole compounds which are important in practice and can advantageously be manufactured by the present process correspond to the general formula

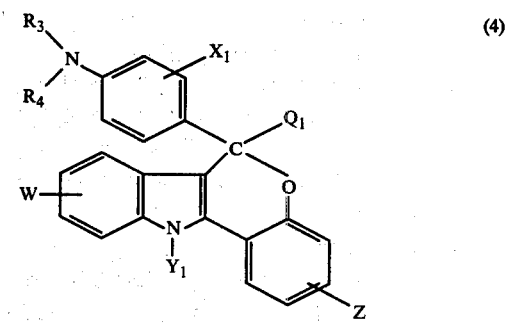

in which $R_3$ and $R_4$ independently of one another denote lower alkyl, phenyl or benzyl and $R_3$ also denotes hydrogen, or $R_3$ and $R_4$, together with the nitrogen atom which links them, denote a pyrrolidino, piperidino or morpholino radical, $X_1$ denotes hydrogen, halogen, methyl or lower alkoxy, $Q_1$ denotes hydrogen, lower alkyl, phenyl, benzyl or the group of the formula

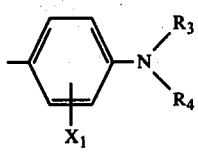
(4a)

W denotes hydrogen, halogen, lower alkyl, lower alkoxy or phenoxy, $Y_1$ denotes hydrogen, lower alkyl, phenyl or benzyl and Z denotes hydrogen, halogen, lower alkyl, lower alkoxy, phenyl or an amino group which is optionally substituted by lower alkyl, benzyl or phenyl.

The chromenoindole compounds of the formula (4) are manufactured from the carbinol compounds and 2-(2'-hydroxyphenyl)-indole compounds corresponding to the symbols $R_3$, $R_4$, $X_1$, $Q_1$, W, $Y_1$ and Z.

In connection with the above substituents in formulae (1) to (4), halogen is, for example, fluorine, bromine or, preferably, chlorine.

The process according to the invention proves to be particularly advantageous for the manufacture of chromenoindole compounds of the general formula

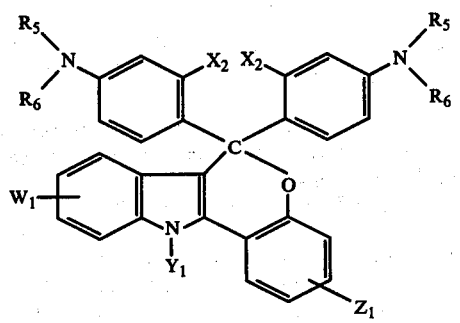
(5)

in which $R_5$ and $R_6$ independently of one another denote lower alkyl or benzyl, $W_1$ denotes hydrogen, chlorine, methyl or methoxy, $X_2$ denotes hydrogen, methyl, methoxy or ethoxy, $Y_1$ denotes hydrogen, lower alkyl, benzyl or phenyl and $Z_1$ denotes hydrogen, chlorine, methyl, tert.-butyl, methoxy or phenyl.

Amongst these compounds of the formula (5), those in which $R_5$ and $R_6$ denote methyl or ethyl, $X_2$ denotes hydrogen, methyl or ethoxy, $W_1$ denotes hydrogen, $Z_1$ denotes hydrogen, methyl or chlorine and $Y_1$ denotes hydrogen, methyl or ethyl are particularly preferred.

The chromenoindole compounds of the formula (5) are manufactured from the benzhydrol compounds and 2-(2'-hydroxyphenyl)-indole compounds corresponding to the symbols $R_5$, $R_6$, $X_2$, $W_1$, $Y_1$ and $Z_1$.

The reaction of the carbinol compounds of the formula (2) with the indole compound of the formula (3) gives a reaction product of the formula

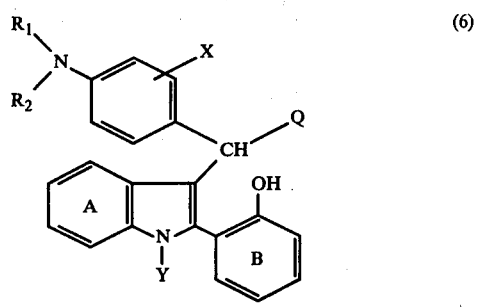
(6)

in which A, B, $R_1$, $R_2$, X, Y and Q have the indicated meaning, water beig eliminated.

This condensation reaction is appropriately carried out in a polar organic solvent, especially in lower aliphatic alcohols, such as, for example, methanol, ethanol or isopropanol, or in ethers, such as, for example, tetrahydrofurane, and preferably in the presence of an acid catalyst. The reaction can already be carried out at room temperature (20° to 25° C). However, it is appropriate to use elevated temperature, preferably 40° to 100° C. Examples of suitable acid catalysts are lower aliphatic carboxylic acids, such as formic acid or acetic acid, and inorganic acids, such as hydrochloric acid, sulphuric acid, phosphoric acid or perchloric acid. The reaction time depends on the temperature and as a rule is between ½ hour and 15 hours.

The resulting reaction product of the formula (6) can be isolated if desired.

The oxidation of the reaction product of the formula (6) to the chromenoindole compounds of the formula (1) is effected with oxidising agents. Examples of suitable oxidising agents are chromates, bichromates, chlorates, chlorites, peroxides, manganese dioxide, lead dioxide, chlorine, bromine, molecular oxygen, air, perborates, permanganates and, in particular, hydrogen peroxide.

The reaction is advantageously carried out in the presence of an organic solvent which does not participate in the oxidation. Suitable solvents are again lower aliphatic alcohols, such as ethanol or isopropanol, ethylene glycol monomethyl ether or ethylene glycol monoethyl ether or lower aliphatic ketones, such as acetone, methyl ethyl ketone or methyl isobutyl ketone.

The best results, in respect of yield and purity of the resulting chromenoindole compounds, are achieved with hydrogen peroxide as the preferred oxidising agent and this is preferably employed in ethanol or isopropanol. For this purpose, the reaction mixture is advantageously rendered alkaline after the condensation reaction of the starting materials of the formulae (2) and (3) has ended. Alkalis such as alkali metal hydroxides, for example sodium hydroxide or potassium hydroxide, alkali metal carbonates or alkali metal bicarbonates, ammonia, alkali metal alcoholates, such as sodium methylate or potassium methylate or sodium ethylate or potassium ethylate, as well as mixtures of these compounds, are suitable for rendering the reaction mixture alkaline. Preferably, the pH value is adjusted to 8 to 13.

The oxidation temperature as a rule depends on the oxidising agent and, above all, on the boiling point of the solvent used. It is appropriately between 20 and 100° C. When hydrogen peroxide is used, the oxidation preferably proceeds at between 60 and 90° C. As a rule, the oxidation takes 1 to 5 hours.

The chromenoindole compounds obtained are isolated, and purified, by known methods.

A great advantage of the process of the present invention is that it can readily be utilised industrially and gives pure end products in very good yields.

A preferred starting material of the formula (2) is 4,4'-bis-(dimethylamino)-benzhydrol ("Michler's Hydrol").

The starting materials of the formula (3) are as a rule manufactured according to the instructions of A. Calvaire and R. Pallaud, Compt. rend. 250 (1960), 3194–95, by reacting a o-hydroxyacetophenone of the formula

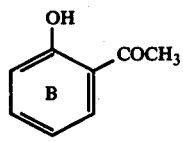

(7)

with a phenylhydrazine of the formula

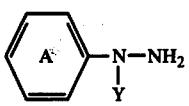

(8)

in which A, B and Y have the indicated meaning, and converting the resulting phenylhydrazone into the desired 2-(2'-hydroxyphenyl)-indole compound by heating in a suitable cyclising agent, for example polyphosphoric acid. When phosphoric acid is used as the cyclising agent, the compounds of the formula (3) can be obtained direct without isolation of the phenylhydrazone which is formed as an intermediate product.

Preferred starting materials of the formula (3) are 2-(2'-hydroxyphenyl)-indole compounds, the hydroxyphenyl radical of which is unsubstituted or ring-substituted by methoxy, tert.-butyl or phenyl or, in particular, by chlorine or methyl.

Examples which may be mentioned of indole compounds which can be used as starting materials of the formula (3) are: 2-(2'-hydroxy-phenyl)-indole, 1-methyl-2-(2'-hydroxyphenyl)-indole, 1-ethyl-2-(2'-hydroxyphenyl)-indole, 2-(2'-hydroxy-5'-methyl-phenyl)-indole, 2-(2'-hydroxy-5'-methoxy-phenyl)-indole, 2-(2'-hydroxy-5'-tert.-butyl-phenyl)-indole, 2-(2'-hydroxy-5'-phenyl-phenyl)-indole and 2-(2'-hydroxy-5'-chlorophenyl)-indole.

The chromenoindole compounds of the formula (1) are usually colourless or slightly coloured. However, they give intense red to blue colour shades when they are brought into contact with a developer, that is to say an electron acceptor.

Typical examples of such developers are attapulgite clay, silton clay, silicon dioxide, bentonite, halloysite, aluminium oxide, aluminium sulphate, aluminium phosphate, zinc chloride, kaolin or any other desired acid clay or organic compounds having an acid reaction, such as, for example, optionally ring-substituted phenols, salicylic acid or salicylates and their metal salts, and also a polymeric material having an acid reaction, such as, for example, a phenolic polymer, an alkylphenol-acetylene resin, a maleic acid/rosin resin or a partially or completely hydrolysed polymer of maleic anhydride with styrene, ethylene, vinyl methyl ether or carboxypolymethylene. Preferred developers are attapulgite clay, silton clay or a phenolformaldehyde resin.

The chromenoindole compounds of the formula (1) display an improved colour intensity and fastness to light both on clay and on phenolic substrates. They are suitable, above all, as colour-forming agents for use in a pressure-sensitive or heat-sensitive recording material, which can be either copying material or documenting material.

A pressure-sensitive material comprises, for example, at least one pair of sheets which contain at least one colour-forming agent of the formula (1), dissolved in an organic solvent, and a solid electron acceptor as the developer. The colour-forming agent gives a coloured marking at the points at which it comes into contact with the electron acceptor.

In order to prevent the colour-forming agent becoming prematurely active in the pressure-sensitive recording material, this agent is as a rule separated from the electron acceptor, for example by incorporating the colour-forming agent into foam-like, sponge-like or honeycombed structures. Preferably, the colour-forming agent is enclosed in micro-capsules which can as a rule be crushed by pressure.

When the capsules are crushed by pressure, for example by means of a pencil, and the solution of the colour-forming agent is thus transferred to an adjacent sheet which is coated with an electron acceptor, a coloured area is produced. This colour results from the dyestuff, formed during this process, which absorbs in the visible region of the electromagnetic spectrum.

The colour-forming agent is preferably encapsulated in the form of solutions in organic solvents. Examples of suitable solvents are preferably non-volatile solvents, for example polyhalogenated diphenyl, such as trichlorodiphenyl, or a mixture thereof with liquid paraffin, and also tricresyl phosphate, di-n-butyl phthalate, dioctyl phthalate, trichlorobenzene, nitrobenzene, trichloroethyl phosphate, petroleum ether, hydrocarbon oils, such as paraffin, alkylated derivatives of diphenyl, naphthalene or triphenyl, terphenyls, partially hydrogenated terphenyl or other chlorinated or hydrogenated, fused, aromatic hydrocarbons.

The capsule walls can be formed uniformly around the droplets of the solution of the colour-forming agent by means of coacervation forces, and the encapsulating material can consist, for example, of gelatine and gum arabic, as described, for example, in U.S. Pat. No. 2,800,457. The capsules can preferably also be formed from an aminoplast or modified aminoplasts by polycondensation, as described in British Patent Specification Nos. 989,264 and 1,156,725.

The micro-capsules containing the colour-forming agents of the formula (1) can be used for the manufacture of pressure-sensitive copying materials of the most diverse known types. The various systems differ from one another essentially in the arrangement of the capsules and of the colour reactants and in the carrier material.

A preferred arrangement is that in which the encapsulated colour-forming agent is applied in the form of a layer to the back of a transfer sheet and the electron acceptor is applied in the form of a layer to the front of a receiving sheet. However, the components can also be used in the paper pulp.

Another arrangement is for the micro-capsules containing the colour-forming agent and the developer to be in or on the same sheet, in the form of one or more individual layers, or in the paper pulp.

The capsules are preferably secured to the carrier by means of an adhesive. Since paper is the preferred carrier material, these adhesives are in the main paper-coating agents, such as gum arabic, polyvinyl alcohol, hydroxymethylcellulose, casein, methylcellulose or dextrin.

The paper used is not only normal papers of cellulose fibres but also papers in which the cellulose fibres are replaced (partially or completely) by fibres of synthetic polymers.

The chromenoindole compounds of the formula (1) can also be used as colour-forming agents in a thermo-reactive recording material. This recording material as a rule contains at least one carrier, a colour-forming agent, a solid electron acceptor and, if appropriate, also a binder. Thermo-reactive recording systems include, for example, heat-sensitive recording and copying materials and papers. These systems are used, for example, for recording information, for example in computers, teleprinters or telex machines, or in measuring instruments. The production of the image (production of the marking) can also be effected manually with a heated pen. Laser beams are a further device for producing markings by means of heat.

The thermo-reactive recording material can be built up in such a way that the colour-forming agent is dissolved or dispersed in a layer of binder and the developer is dissolved or dispersed in the binder in a second layer. Another possibility is for both the colour-forming agent and the developer to be dispersed in one layer. The binder is softened by means of heat in specific areas and at these points, to which heat is applied, the colour-forming agent comes into contact with the electron acceptor and the desired colour develops immediately.

Suitable developers are the same electron acceptor substances as are used in pressure-sensitive papers.

Film-forming binders which can be melted are preferably used to manufacture the thremo-reactive recording material. These binders are usually soluble in water, whilst the chromenoindole compounds and the developer are insoluble in water. The binder should be capable of dispersing and fixing the colour-forming agent and tHe developer at room temperature.

The binder softens or melts under the action of heat, so that the colour-forming agent comes into contact with the developer and can form a colour. Examples of binders which are soluble in water or at least swellable in water are hydrophilic polymers, such as polyvinyl alcohol, polyacrylic acid, hydroxyethylcellulose, methylcellulose, carboxymethylcellulose, polyacrylamide, polyvinylpyrrolidone, gelatine and starch.

When the colour-forming agent and the developer are present in two separate layers, binders which are insoluble in water, that is to say binders which are soluble in non-polar solvents, such as, for example, natural rubber, synthetic rubber, chlorinated rubber, alkyd resins, polystyrene, styrene/butadiene copolymers, polymethyl methacrylate, ethylcellulose, nitrocellulose and polyvinylcarbazole, can be used. An arrangement in which the colour-forming agent and the developer are contained in a water-soluble binder in one layer is preferred.

The thermo-reactive layers can contain further additives. In order to improve the whiteness, to facilitate printing of the papers and to prevent the heated pen from adhering, these layers can contain, for example, talc, $TiO_2$, ZnO or $CaCO_3$, or also organic pigments, such as, for example, urea-formaldehyde polymers. In order to ensure that the colour is formed only within a limited temperature range, substances such as urea, thiourea, acetanilide, phthalic anhydride or other corresponding fusible products which induce simultaneous melting of the colour-forming agent and the developer, can be added.

In the examples which follow, the percentages quoted relate to weight, unless otherwise indicated.

EXAMPLE 1

A mixture of 27.0 g of 4,4'-bis-(dimethylamino)-benzhydrol ("Michler's Hydrol"), 21.0 g of 2-(2'-hydroxyphenyl)-indole, 3 ml of glacial acetic acid and 300 ml of ethanol is heated under reflux for 5 hours. 4.2 g of potassium hydroxide in 25 ml of ethanol and 30 ml of 35% strength hydrogen peroxide solution in 100 ml of ethanol are then added in the course of 2 hours. After a further 2 hours under reflux, the reaction mixture is cooled to 35° C. 300 ml of water are then allowed to run in dropwise. The mixture is cooled to room temperature and the precipitate which has formed is then filtered off and dried. This gives 42.5 g (92.5% of theory) of a compound of the formula

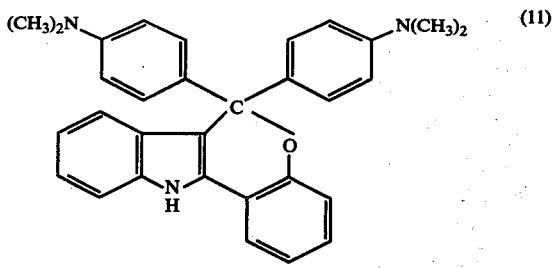

The product can be purified by stirring in 200 ml of methanol and subsequently rinsing the precipitate with a further 200 ml of methanol. The compound of the formula (11) has a melting point of 145–150° C (decomposition). On silton clay, this coolour-forming agent develops a blue colour with a λmax of 620 nm.

The reaction product obtained in Example 1 from 4,4'-bis-(dimethylamino)-benzhydrol and 2-(2'-hydroxyphenyl)-indole can be isolated in the following way:

After the reaction under reflux has ended, the reaction product is cooled to room temperature and the supernatant liquor is decanted off. The residue is stirred at room temperature with 1 N sodium hydroxide solution, whereupon a granular, bluish precipitate forms. This is filtered off, washed with water and dried. 38.0 g (82.3% of theory) of a compound of the formula

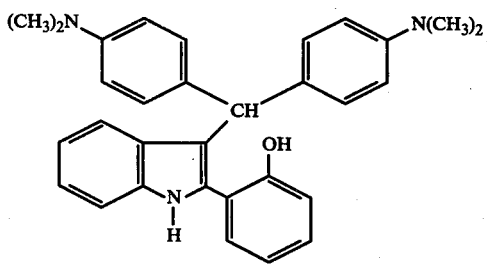

with a melting point of 159–162° C (decomposition) are obtained.

EXAMPLE 2

If, in Example 1, the 2-(2'-hydroxyphenyl)-indole is replaced by 22.3 g of 2-(2'-hydroxy-5'-methylphenyl)-indole and in other respects the precedure followed is as described in Example 1, 45.1 g (95% of theory) of a compound of the formula

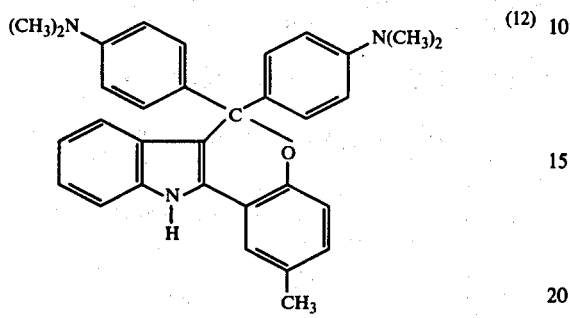

are obtained. This compound melts at 151–155° C (decomposition). On silton clay, this colour-forming agent develops a blur colour with a λ max of 615 nm.

EXAMPLE 3

If, in Example 1, the 2-(2'-hydroxy-phenyl)-indole is replaced by 24.4 g of 2-(5'-chloro-2'-hydroxyphenyl)-indole and in other respects the precedure followed is as described in Example 1, 41.9 g (84.8% of theory) of a compound of the formula

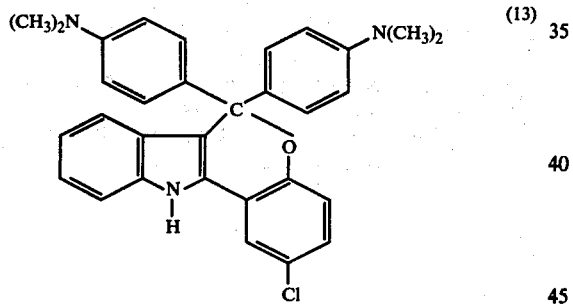

are ontained. This compoun has amelting point of 165–170° C (decomposition). On silton clay, it develops a blue colour with a λ max of 620 nm.

EXAMPLE 4

If, in Example 1, the 4,4'-bis-(dimethylamino)-benzhydrol is replaced by 22.7 g of 4-dimethylamino-benzhydrol and in other respects the precedure followed is as described in Example 1, 33.4 g (80.2% of theory) of a compound of the formula

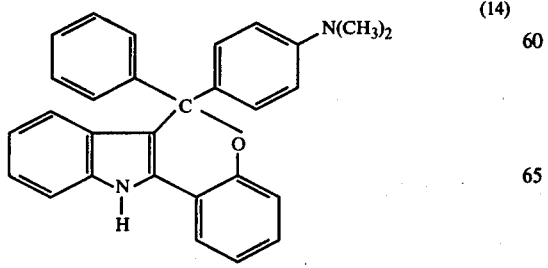

which melts at 229–231° C are obtained. On silton clay this colour-forming agent develops a blue colour with a λ max of 600 nm.

What is claimed is:

1. A process for the manufacture of a chromenoindole compound of the formula

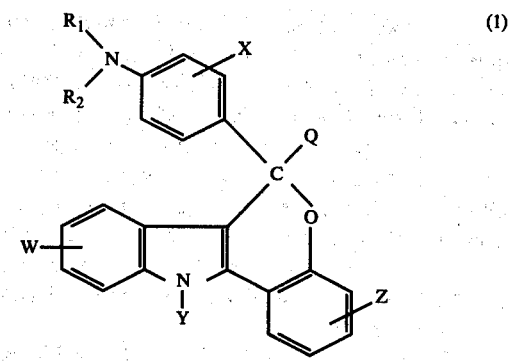

wherein $R_1$ and $R_2$ independently of one another represent hydrogen, alkyl which has at most 12 carbon atoms and is unsubstituted or substituted by halogen, nydroxyl, cyano or lower alkoxy, cycloalkyl, phenyl, benzyl or phenyl or benzyl which are substituted by halogen, lower alkyl or lower alkoxy, or $R_1$ and $R_2$, together with the nitrogen atom which links them, represent a 5-membered or 6-membered heterocylic radical, Q represents hydrogen, lower alkyl, phenyl, benzyl or a group of the formula (1a) or (1b)

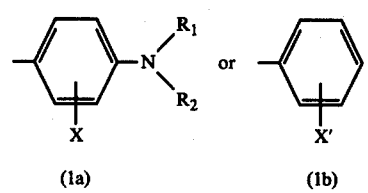

X and X' each represent hydrogen, halogen, lower alkyl or lower alkoxy,

Y represents hydrogen, alkyl of 1 to 12 carbon atoms, phenyl or benzyl and W and Z independently of one another are hydrogen, halogen, nitro, lower alkyl, lower alkoxy, phenyl, phenoxy, amino or amino which is substituted by lower alkyl, phenyl or benzyl, which process comprises the steps of reacting a carbinol compound of the formula

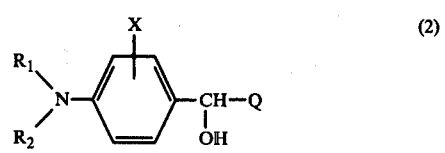

with a (2-(2'-hydroxyphenyl)-indole compound of the formula

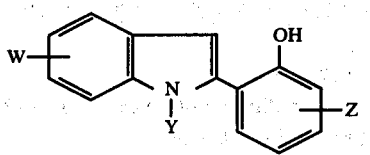 (3)

in the presence of an acid catalyst selected from the group consisting of lower aliphatic carboxylic acids or inorganic acids at a temperature from 20 to 100° C for a period of time from 0.5 hour to 15 hours and oxidising the reaction product with an oxidising agent selected from the group consisting of chromates, bichromates, chlorates, chlorites, peroxides, manganese dioxide, lead dioxide, chlorine, bromine, molecular oxygen, air, perborates, permanganates or hydrogen peroxide, at a temperature from 20 to 100° C and for a period of time from 1 hour to 5 hours.

2. The process of claim 1, wherein $R_1$ and $R_2$ independently of one another represent lower alkyl, phenyl or benzyl and $R_1$ also represents hydrogen, or $R_1$ and $R_2$ together with the nitrogen atom which links them, represent a pyrrolidino, piperidino or morpholino radical, X represents hydrogen, halogen, methyl or lower alkoxy, Q represents hydrogen, lower alkyl, phenyl, benzyl or the group of the formula

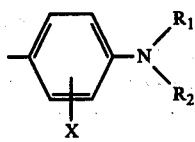

W represents hydrogen, halogen, lower alkyl, lower alkoxy or phenoxy,

Y represents hydrogen, lower alkyl, phenyl or benzyl and

Z represents hydrogen, halogen, lower alkyl, lower alkoxy, phenyl, amino or amino which is substituted by lower alkyl, benzyl or phenyl.

3. The process of claim 1, wherein Q is the group of formula (1a), wherein, $R_1$ and $R_2$ independently of one another represent lower alkyl or benzyl, W represents hydrogen, chlorine, methyl or methoxy, X represents hydrogen, methyl, methoxy or ethoxy, Y represents hydrogen, lower alkyl, benzyl or phenyl and Z represents hydrogen, chlorine, methyl, tert.-butyl, methoxy or phenyl.

4. The process of claim 3, wherein $R_1$ and $R_2$ represent methyl or ethyl,

X represents hydrogen, methyl or ethoxy,

W represents hydrogen,

Z represents hydrogen, methyl or chlorine and

Y represents hydrogen, methyl or ethyl.

5. The process of claim 1, wherein the starting material of the formula (2) is 4,4'-bis-(dimethylamino)-benzhydrol.

6. The process of claim 1, wherein Z is hydrogen, chlorine, methyl, methoxy, tert.-butyl or phenyl.

7. The process of claim 1, wherein Z is hydrogen, chlorine or methyl.

8. The process of claim 1, wherein the oxidising agent is hydrogen peroxide.

9. The process of claim 8, wherein the oxidation is carried out with hydrogen peroxide in an alkaline medium.

10. The process of claim 8, wherein hydrogen peroxide in ethanol or isopropanol is used.

* * * * *